United States Patent
Lim et al.

(10) Patent No.: US 7,452,376 B2
(45) Date of Patent: Nov. 18, 2008

(54) FLEXIBLE, NON-PLANAR ANNULOPLASTY RINGS

(75) Inventors: Jyue Boon Lim, Minneapolis, MN (US); William M Sutton, Minnetonka, MN (US)

(73) Assignee: St. Jude Medical, Inc., St. Paul, MN (US)

( * ) Notice: Subject to any disclaimer, the term of this patent is extended or adjusted under 35 U.S.C. 154(b) by 242 days.

(21) Appl. No.: 11/126,779

(22) Filed: May 10, 2005

(65) Prior Publication Data

US 2005/0256569 A1 Nov. 17, 2005

Related U.S. Application Data

(60) Provisional application No. 60/571,419, filed on May 14, 2004.

(51) Int. Cl.
A61F 2/24 (2006.01)
(52) U.S. Cl. .................................................. 623/2.36
(58) Field of Classification Search ........ 623/2.36–2.38
See application file for complete search history.

(56) References Cited

U.S. PATENT DOCUMENTS

| | | | |
|---|---|---|---|
| 3,656,185 A | 4/1972 | Carpentier | |
| 4,042,979 A | 8/1977 | Angell | |
| 4,055,861 A | 11/1977 | Carpentier et al. | |
| 4,703,676 A | 11/1987 | Mayer | |
| 4,743,253 A | 5/1988 | Magladry | |
| 4,865,600 A | 9/1989 | Carpentier et al. | |
| 4,932,965 A | 6/1990 | Phillips | |
| 5,061,277 A | 10/1991 | Carpentier et al. | |
| 5,089,015 A | 2/1992 | Ross | |
| 5,104,407 A * | 4/1992 | Lam et al. ................. | 623/2.36 |
| 5,306,296 A | 4/1994 | Wright et al. | |
| 5,350,420 A | 9/1994 | Cosgrove et al. | |
| 5,403,305 A | 4/1995 | Sauter et al. | |
| 5,415,667 A | 5/1995 | Frater | |
| 5,522,884 A | 6/1996 | Wright | |
| 5,607,471 A | 3/1997 | Seguin et al. | |
| 5,669,919 A | 9/1997 | Sanders et al. | |
| 5,800,531 A | 9/1998 | Cosgrove et al. | |
| 5,814,097 A | 9/1998 | Sterman et al. | |
| 5,814,101 A | 9/1998 | Wallner et al. | |

(Continued)

FOREIGN PATENT DOCUMENTS

EP 0 338 994 10/1989

(Continued)

OTHER PUBLICATIONS

Belcher, J.R., "The Surgical Treatment of Mitral Regurgitation", British Heart Journal vol. 26, pp. 513-5223 (1964).

(Continued)

*Primary Examiner*—William H. Matthews
(74) *Attorney, Agent, or Firm*—Ropes & Gray LLP

(57) ABSTRACT

An annuloplasty ring (for use as a heart valve prosthesis) has a non-planar shape and different lateral flexibilities at different points as one proceeds annularly around the ring. These different lateral flexibilities may be achieved in different ways such as by changing the material and/or cross-sectional size, shape, or other stiffness-imparting characteristics of the cross section.

19 Claims, 7 Drawing Sheets

U.S. PATENT DOCUMENTS

| | | | |
|---|---|---|---|
| 5,824,066 | A | 10/1998 | Gross et al. |
| 5,843,177 | A | 12/1998 | Vanney et al. |
| 5,888,240 | A | 3/1999 | Carpentier et al. |
| 5,972,030 | A | 10/1999 | Garrison et al. |
| 6,001,127 | A | 12/1999 | Schoon et al. |
| 6,019,739 | A | 2/2000 | Rhee et al. |
| 6,143,024 | A | 11/2000 | Campbell et al. |
| 6,187,040 | B1 | 2/2001 | Wright |
| 6,214,043 | B1 | 4/2001 | Krueger et al. |
| 6,217,610 | B1 | 4/2001 | Carpentier et al. |
| 6,231,602 | B1 | 5/2001 | Carpentier et al. |
| 6,283,993 | B1 | 9/2001 | Cosgrove et al. |
| 6,319,280 | B1 | 11/2001 | Schoon |
| 6,368,348 | B1 | 4/2002 | Gabbay |
| 6,391,054 | B2 | 5/2002 | Carpentier et al. |
| 6,406,492 | B1 | 6/2002 | Lytle |
| 6,409,758 | B2 | 6/2002 | Stobie et al. |
| 6,451,054 | B1 | 9/2002 | Stevens |
| 6,564,805 | B2 | 5/2003 | Garrison et al. |
| 6,602,289 | B1 | 8/2003 | Colvin et al. |
| 6,689,163 | B2 | 2/2004 | Lytle |
| 6,702,852 | B2 | 3/2004 | Stobie et al. |
| 6,719,786 | B2 | 4/2004 | Ryan et al. |
| 6,726,717 | B2 | 4/2004 | Alfieri et al. |
| 6,730,121 | B2 | 5/2004 | Ortiz et al. |
| 6,749,630 | B2 | 6/2004 | McCarthy et al. |
| 6,786,924 | B2 | 6/2004 | Ryan et al. |
| 2002/0129820 | A1 | 9/2002 | Ryan et al. |
| 2002/0133180 | A1 | 9/2002 | Ryan et al. |
| 2002/0173844 | A1 | 11/2002 | Alfieri et al. |
| 2002/0183839 | A1 | 12/2002 | Garrison et al. |
| 2003/0045929 | A1 | 3/2003 | McCarthy et al. |
| 2003/0050693 | A1 | 3/2003 | Quijano et al. |
| 2003/0093148 | A1* | 5/2003 | Bolling et al. ............. 623/2.36 |
| 2003/0144732 | A1 | 7/2003 | Cosgrove et al. |
| 2003/0176916 | A1 | 9/2003 | Ryan et al. |
| 2003/0176917 | A1 | 9/2003 | Ryan et al. |
| 2003/0199975 | A1 | 10/2003 | Gabbay |
| 2004/0006384 | A1 | 1/2004 | McCarthy |
| 2004/0019357 | A1 | 1/2004 | Campbell et al. |
| 2004/0034410 | A1 | 2/2004 | Holmberg |
| 2004/0133273 | A1 | 7/2004 | Cox |
| 2004/0186564 | A1 | 9/2004 | Ryan et al. |
| 2004/0249453 | A1* | 12/2004 | Cartledge et al. .......... 623/2.37 |

FOREIGN PATENT DOCUMENTS

| | | |
|---|---|---|
| EP | 0 375 181 | 6/1990 |
| EP | 0 495 417 | 7/1992 |
| EP | 0 595 791 | 5/1994 |
| EP | 1 034 753 | 9/2000 |
| WO | WO 91/17721 | 7/1991 |
| WO | WO 99/04730 | 2/1999 |
| WO | WO 02/074197 | 9/2002 |
| WO | WO 03/020178 | 3/2003 |
| WO | WO 03/053289 | 7/2003 |

OTHER PUBLICATIONS

Carpentier, A., "La Valvuloplastie Reconstitutive: Une Nouvelle Technique de Valvuloplastie Mitrale", Technique Chirugicale, No. 7, pp. 251-255 (1969).

Carpentier, A., et al., "A New Reconstructive Operation for Correction of Mitral and Tricuspid Insufficiency", The Journal of Thoracic and Cardiovascular Surgery, vol. 61, No. 1, pp. 1-13 (1971).

Duran, C.G., et al., "Clinical and Hemodynamic Performance of a Totally Flexible Prosthetic Ring for Atrioventricular Valve Reconstruction", The Annals of Thoracic Surgery, vol. 22, No. 5, pp. 458-463 (1976).

Cooley, D.A., et al., "Mitral Leaflet Prolapse: Surgical Treatment using a Posterior Annular Collar Prosthesis", Cardiovascular Diseases Bulletin of the Texas Heart Institute, vol. 3, No. 4, pp. 438-443 (1976).

Duran, C.G., "Reconstructive procedures of the Mitral Valve Including Ring Annuloplasty", Modern Technics in Surgery, 20 (1979).

Erk, M.K., "Morphological and Functional Reconstruction of the Mitral Valve: A New Annuloplastic Procedure," Texas Heart Institute Journal, vol. 9, pp. 329-334 (1982).

Castells, E., et al., "Long-Term Results With the Puig Massana-Shiley Annuloplasty Ring", The Journal of Cardiovascular Surgery, Abstracts, vol. 24 No. 4, p. 387 (1983).

Alonso-Lej, F., "The 'dynamic' mitral ring: A new concept in treating mitral insufficiency", Recent Progress in Mitral Valve Disease, pp. 45 and 443-449 (1984).

Henze, A., et al., "The Adjustable Half-Moon: An Alternative Device for Tricuspid Valve Annuloplasty", Scandinavian Journal of Thoracic and Cardiovascular Surgery, vol. 18, pp. 29-32 (1984).

Reece, I.J., et al., "Surgical Treatment of Mitral Systolic Click Syndrome: Results in 37 Patients", The Annals of Thoracic Surgery, vol. 39, No. 2, pp. 155-158 (1985).

Morse, D., et al., "Cardiac Valve Identification Atlas and Guide", Chapter 10 in Guide to Prosthetic Cardiac Valves, edited by Dryden Morse, Robert M. Steiner, and Javier Fernandez, Springer-Verlag New York Inc. (1985).

Durán, C.M.G., et al., "A New Absorbable Annuloplasty Ring in the Tricuspid Position: An Experimental Study", The Thoracic and Cardiovascular Surgeon, vol. 34, No. 6, pp. 377-379 (1986).

Levine, R.A., et al., "The Relationship of Mitral Annular Shape to the Diagnosis of Mitral Valve Prolapse", Circulation, vol. 75, No. 4, pp. 756-767 (1987).

Murphy, J. P. et al., "The Puig-Massana-Shiley Annuloplasty Ring for Mitral Valve Repair: Experience in 126 Patients," The Annals of Thoracic Surgery, vol. 43, pp. 52-58 (1987).

Ahmadi, A., et al., "Hemodynamic Changes Following Experimental Production and Correction of Acute Mitral Regurgitation With An Adjustable Ring Prosthesis", The Thoracic and Cardiovascular Surgeon, vol. 36, No. 6, pp. 313-319 (1988).

Duran, C.G., et al., "Stability of Mitral Reconstructive Surgery at 10-12 Years for Predominantly Rheumatic Valvular Disease", Circulation Supplement I, Vol. 78, No. 3, pp. I-91-I-96 (1988).

Gregori, F., Jr., et al., "Um Novo Modelo De Anel Protetico Para Pacientes Com Insuficiencia Valvar Mitral. Relato de Dois Casos", Arquivos Brasileiros de Cardiologia, vol. 50, No. 6, pp. 417-420 (1988).

Shumway, S.J., et al., "A 'Designer' Annuloplasty Ring for Patients with Massive Mitral Annular Dilation", The Annals of Thoracic Surgery, vol. 46, No. 6, pp. 695-696 (1988).

Erk, M.K., et al., "Semi-frame Mitral Annuloplasty", Cardiac Reconstructions pp. 157-163 (1989).

Chachques, J.C., et al., "Absorbable Rings for Pediatric Valvuloplasty: Preliminary Study", Supplement IV to Circulation, vol. 82, No. 5, pp. IV-82-IV-88 (1990).

Deloche, A., et al., "Valve Repair With Carpentier Techniques", The Journal of Thoracic and Cardiovascular Surgery, vol. 99, No. 6, pp. 990-1002 (1990).

Duran, C.M.G., et al., "Valve Repair in Rheumatic Mitral Disease", Supplement to Circulation vol. 84, No. 5, pp. III 125-III 132 (1990).

Fundarò, P., et al., "Polytetrafluoroethylene Posterior Annuloplasty for Mitral Regurgitation", The Annals of Thoracic Surgery, Correspondence, vol. 50, No. 1, pp. 165-166 (1990).

Hendren, W.G., et al., "Mitral Valve Repair for Ischemic Mitral Insufficiency", The Annals of Thoracic Surgery, vol. 52, pp. 1246-1252 (1991).

Salati, M., et al., "Posterior Pericardial Annuloplasty: A Physiological Correction?", European Journal of Cardio-Thoracic Surgery, vol. 5, pp. 226-229 (1991).

Cooley, D.A., "Ischemic Mitral Insufficiency", Cardiac Surgery: State of the Art Reviews, vol. 6, No. 2, pp. 237-249 (1992).

Martin, S. L., et al., "Echocardiographic Evaluation of Anuloplasty Rings: Comparison of Continuity Equation and Pressure Half-Time Methods", Journal of The American Society of Echocardiography, vol. 5, No. 3, p. 322 (1992).

Суδарикоβ, В.Ф, et al., "АhhyПоПactnka TpnkycПnoaПhoГo KПa Паhа PеГyПnpyembim ПоПyкоПbuom Поо KоhtpоПem YpесПnweboоhоn ExоkapоnоГpaβnn", KоПIIektnb Abtopob (1992).

Cooley, D.A., et al., "A Cost-Effective Dacron Annuloplasty Ring", The Annals of Thoracic Surgery, Vol. 56, pp. 185-186 (1993).

Pellegrini, A., et al., "Posterior Annuloplasty in the Surgical Treatment of Mitral Insufficiency", The Journal of Heart Valve Disease, vol. 2, pp. 633-638 (1993).

Salvador, L. et al., "The Pericardium Reinforced Suture Annuloplasty: Another Tool Available for Mitral Annulus Repair," Journal of Cardiac Surgery, vol. 8, pp. 79-84 (1993).

Victor, S. et al., "Truly Flexible D-shaped Autogenous Pericardial Ring for Mitral Annuloplasty," The Annals of Thoracic Surgery, vol. 56, pp. 179-180 (1993).

Gorton, M.E. et al., "Mitral Valve Repair Using a Flexible and Adjustable Annuloplasty Ring," The Annals of Thoracic Surgery, vol. 55, pp. 860-863 (1993).

Salati, M. et al., "Annular Remodelling With Pericardial Reinforcement: Surgical Technique and Early Results," The Journal of Heart Valve Disease, vol. 2, pp. 639-641 (1993).

Gregori, F., et al., "Mitral Valvuloplasty With A New Prosthetic Ring", Official Journal of the European Association for Cardio-thoracic surgery, vol. 8, No. 4, pp. 168-172 (1994).

Carpentier, A.F., et al., The 'Physio-Ring': An Advanced Concept in Mitral Valve Annuloplasty, Ann. Thorac. Surg. vol. 60, No. 5, pp. 1177-1186 (1995).

Melo, J.Q., et al. "Surgery for Acquired Heart Disease: Atrioventricular Valve Repair Using Externally Adjustable Flexible Rings", The Journal of Thoracic and Cardiovascular Surgery No. 110, pp. 1333-1337 (1995).

Bolling, S.F., et al., "Surgery For Acquired Heart Disease", The Journal of Thoracic and Cardiovascular Surgery, vol. 109, No. 4, pp. 676-683 (1995).

Cosgrove, D.M. III, et al, "Initial Experience With the Cosgrove-Edwards Annuloplasty System", The Annals of Thoracic Surgery, vol. 60, pp. 499-504 (1995).

Katz, N.M., "Current Surgical Treatment of Valvular Heart Disease", American Family Physician, vol. 52, No. 2, pp. 559-568 (1995).

Ghosh, P.K., "Mitral Annuloplasty: A Right-Side View," The Journal of Heart Valve Disease, vol. 5, pp. 286-293 (1996).

Vongpatanasin, W., et al., "Prosthetic Heart Valves", The New England Journal of Medicine, vol. 335, No. 6, pp. 407-416 (1996).

Kasegawa, H., et al., "Physiologic Remodeling Annuloplasty to Retain the Shape of the Anterior Leaflet: A New Concept in Mitral Valve Repair", The Journal of Heart Valve Disease, vol. 6, pp. 604-607 (1997).

Kurosawa, H., et al., "Mitral Valve Repair by Carpentier-Edwards Physio Annuloplasty Ring", The Japanese Journal of Thoracic and Cardiovascular Surgery, vol. 47, pp. 355-360 (1999).

Smolens, I., et al., "Current Status of Mitral Valve Reconstruction in Patients with Dilated Cardiomyopathy", Ital. Heart J., vol. 1, No. 8, pp. 517-520 (2000).

Lachmann, J., MD, et al., "Mitral Ring Annuloplasty: An Incomplete Correction of Functional Mitral Regurgitation Associated with Left Ventricular Remodeling", Current Cardiology Reports, vol. 3, pp. 241-246 (2001).

Rubenstein, F., et al., "Alternatives in Selection of Rings for Mitral Annuloplasty", Current Opinion in Cardiology, vol. 16, No. 2, pp. 136-139 (2001).

Bolling, S.F., "Mitral Reconstruction in Cardiomyopathy", The Journal of Heart Valve Disease, vol. 11, Suppl. 1, pp. S26-S31 (2002).

Ogus, T.N., et al., "Posterior Mitral Annuloplasty with an Adjustable Homemade Ring", Journal of Cardiac Surgery, vol. 17, No. 3, pp. 226-228 (2002).

Kaye, D.M., et al., "Feasibility and Short-Term Efficacy of Percutaneous Mitral Annular Reduction for the Therapy of Heart Failure—Induced Mitral Regurgitation, Circulation, Brief Rapid Communication", No. 108, pp. 1795-1797 (2003).

\* cited by examiner

FLEXIBLE, NON-PLANAR ANNULOPLASTY RINGS

This application claims the benefit of U.S. provisional patent application No. 60/571,419, filed May 14, 2004, which is hereby incorporated by reference herein in its entirety.

BACKGROUND OF THE INVENTION

Annuloplasty rings for use as heart valve prostheses are well known as shown, for example, by Alfieri et al. U.S. patent application publication U.S. 2002/0173844 A1 and Bolling et al. U.S. patent application publication U.S. 2003/0093148 A1. Most such rings are substantially planar (see, for example, the above-mentioned Alfieri et al. reference). Recently, an interest in non-planar (e.g., saddle-shaped) rings has developed (see, for example, the above-mentioned Bolling et al. reference). The known non-planar rings tend to be substantially uniformly rigid. It would be desirable to have non-planar rings that are not uniformly rigid.

SUMMARY OF THE INVENTION

In accordance with this invention an annuloplasty ring has a non-planar shape and has different lateral flexibilities at different points as one proceeds annularly around the ring. These different laterally flexibilities may be achieved in various ways. For example, the cross section of the ring (or its main structural member(s)) may change as one proceeds annularly around the ring. As another example, the material of the ring (or its main structural member(s)) may change as one proceeds annularly around the ring. As still another example, other cross sectional properties of the ring may change to change lateral flexibility as one proceeds annularly around the ring.

Further features of the invention, its nature and various advantages, will be more apparent from the accompanying drawings and the following detailed description of the preferred embodiments.

BRIEF DESCRIPTION OF THE DRAWINGS

FIG. 1 is taken along the line 1-1 in FIG. 2.

FIG. 3 is taken along the line 3-3 in FIG. 4.

FIG. 5 is taken along the line 5-5 in FIG. 6.

FIG. 7 is sectional to reveal interior structure of what is shown.

DETAILED DESCRIPTION

Figure 1:
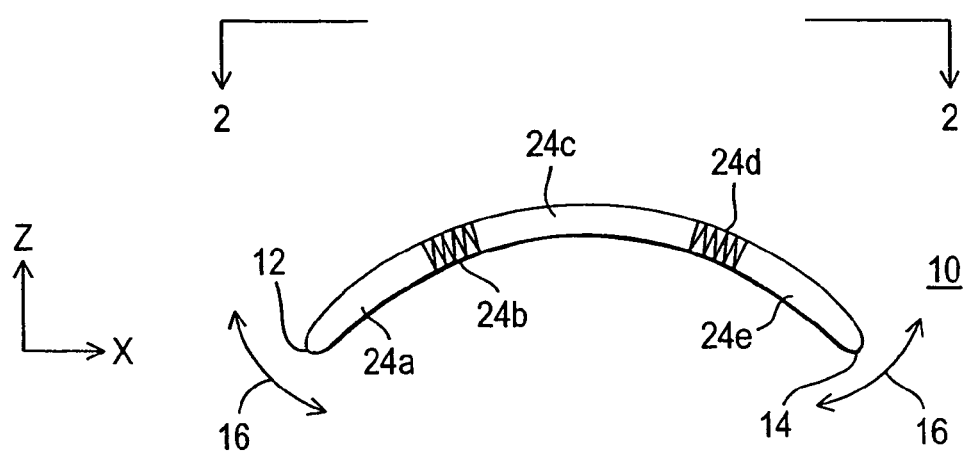
FIG. 1 is a simplified elevational view of an illustrative embodiment of an annuloplasty ring constructed in accordance with the invention.
Figure 2:
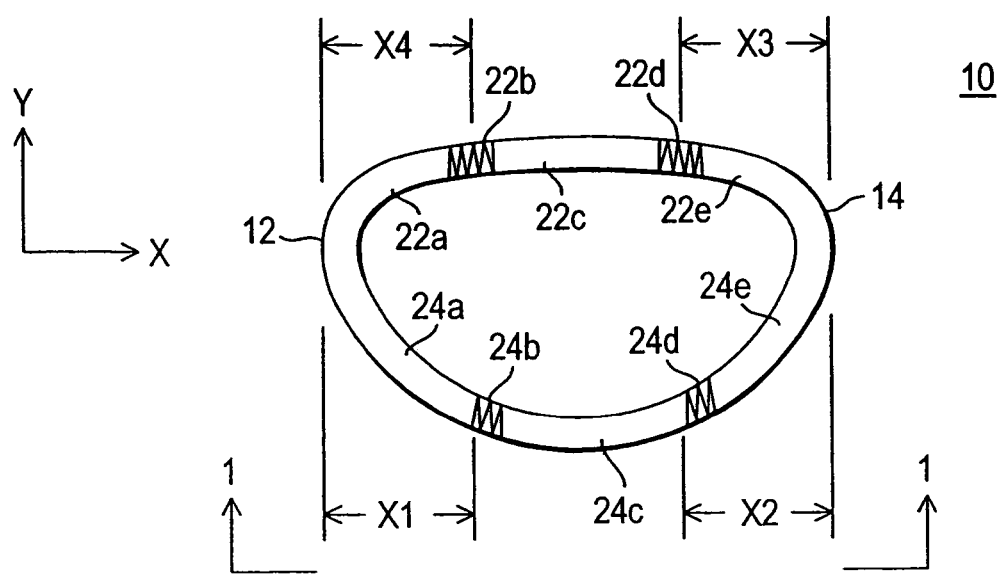
FIG. 2 is a simplified plan view taken along the line 2-2 in FIG. 1.

As shown in FIGS. 1 and 2, an illustrative annuloplasty ring 10 in accordance with the invention is approximately D-shaped in plan view (see FIG. 2), but approximately saddle-shaped when all three dimensions (x, y, and z) are considered. The endpoints 12 and 14 of the greatest width of ring 10 along the x axis are also the lowest points of the saddle shape. Points 12 and 14 may be thought of as lying in a plane that is parallel to any plan view (e.g., FIG. 2) of the ring. The ring has two segments that connect points 12 and 14 to one another. One of these segments is in the upper portion of FIG. 2, and the other of these segments is in the lower portion of FIG. 2. If ring 10 were to be used as a mitral heart valve prosthesis, the ring would be implanted with points 12 and 14 adjacent the commissures of the valve, the upper segment in FIG. 2 adjacent the anterior side of the valve, and the lower segment in FIG. 2 adjacent the posterior side of the valve. The upward direction in FIG. 1 would also be generally upward when the patient was standing upright.

Each of the above-mentioned segments of ring 10 arches upwardly out of the plan-view-parallel plane that includes points 12 and 14 (see FIG. 1). Adjacent each of points 12 and 14 ring 10 is preferably smoothly concave when viewed from above (as in FIG. 2). For reference, the y axis is perpendicular to the x axis in a plan view plane. The z axis is perpendicular to the plan view plane (see FIG. 1).

In the illustrative embodiment shown in FIGS. 1 and 2, each of the above-mentioned segments of ring 10 extending between points 12 and 14 includes two annularly spaced portions that are more laterally flexible than the other portions of the segment. For example, in the upper segment these more flexible portions are at 22b and 22d. In the lower segment, these more flexible portions are at 24b and 24d. As used herein, lateral flexibility refers to flexibility transverse to the local longitudinal axis (in the annular direction) of ring 10. Another way to describe this is as flexibility transverse to a local tangent (again in the annular direction) to ring 10.

In the particular example shown in FIGS. 1 and 2 all of more flexible portions 22b, 22d, 24b, and 24d are equally spaced in the x direction from the nearer of points 12 and 14. In other words, in this example all of dimensions x1, x2, x3, and x4 are the same. This is not necessarily the case, however, and in other embodiments these dimensions can have different values. For example, another such embodiment may have x1=x4 and x2=x3 but x1 not equal to x2. As another example, x1 and x2 may be equal, x3 and x4 may be equal, but x1 may not equal x4.

Note that the arrangement of FIGS. 1 and 2 produces a structure having two relatively inflexible wings 22a/24a and 22e/24e that are connected relatively flexibly (by portions 22b, 22d, 24b, and 24d) to a relatively inflexible center section (portions 22c and 24c). Wings 22a/24a and 22e/24e can flex up and down in the z direction (as indicated by arrows 16 in FIG. 1), giving ring 10 flexibility in that direction. Such up and down flexing of the wings changes the dimension of the ring in the x direction. This contributes to flexibility of the ring in the x direction. The flexibility of portions 22b/d and 24b/d also contributes to ring flexibility in the y direction.

Figure 3:
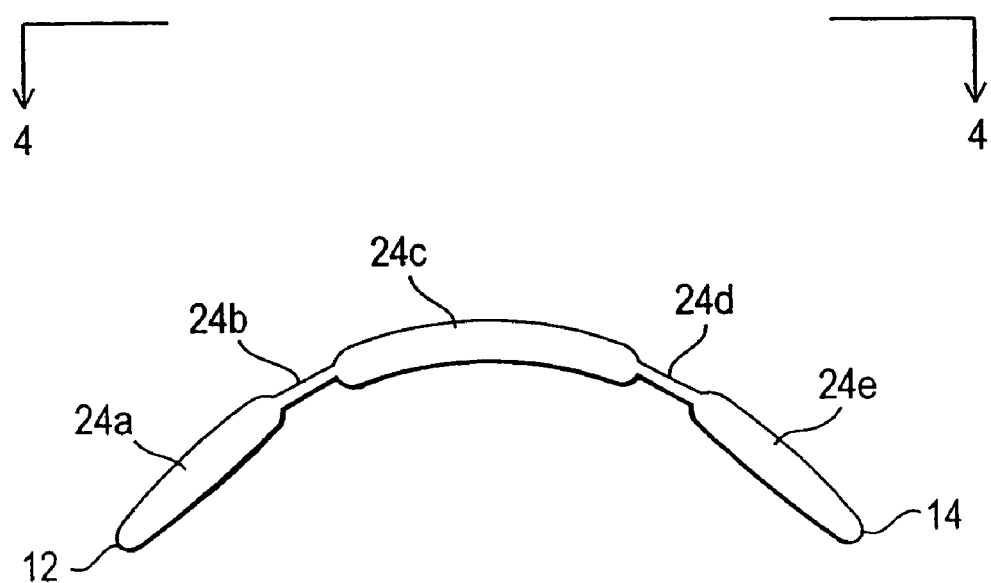
FIG. 3 is similar to FIG. 1 for a particular illustrative embodiment in accordance with the invention.
Figure 4:
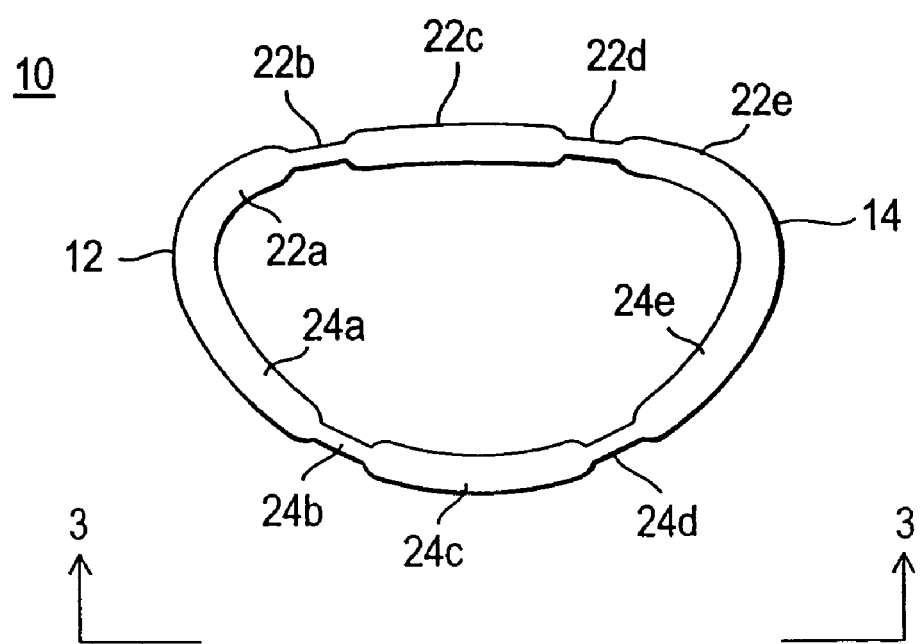
FIG. 4 is a simplified plan view taken along the line 4-4 in FIG. 3.

Portions 22b/d and 24b/d of greater lateral flexibility can be produced in various ways. For example, these portions can be made of a material that has greater lateral flexibility (less lateral stiffness) than a material that is used for other portions of ring 10. FIGS. 3 and 4 show another example in which the same material can be used for all portions of ring 10, but portions 22b/d and 24b/d have smaller cross section than other portions of the ring. The smaller cross section of portions 22b/d and 24b/d makes these portions weaker and therefore more laterally flexible.

Figure 5:
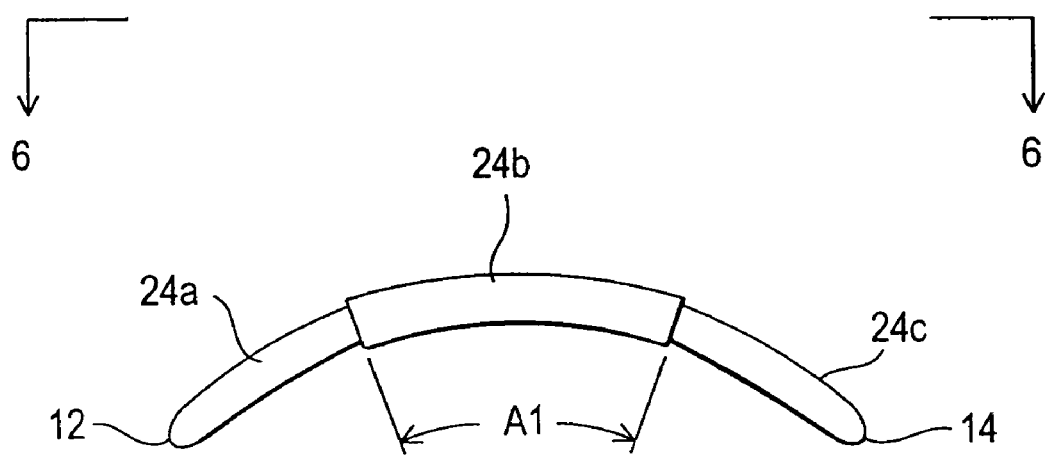
FIG. 5 is similar to FIG. 1 for another illustrative embodiment in accordance with the invention.
Figure 6:
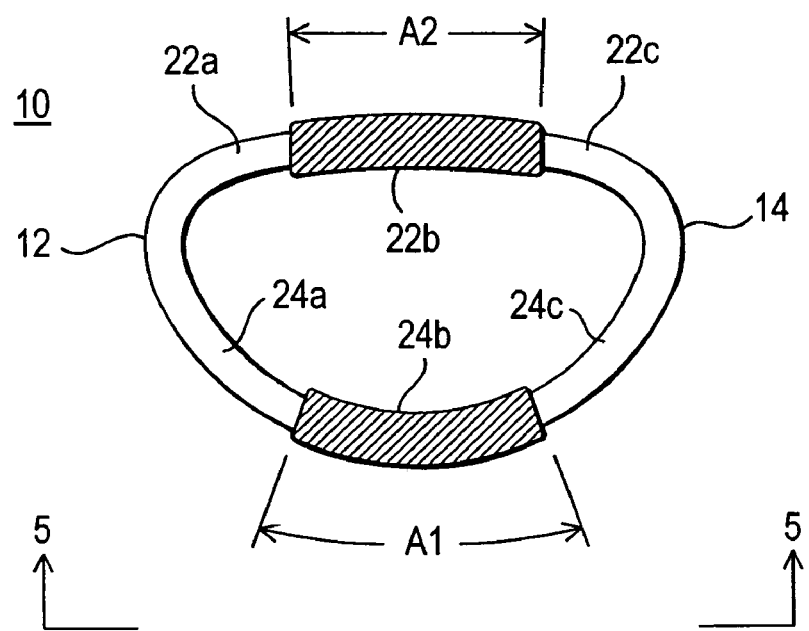
FIG. 6 is a simplified plan view taken along the line 6-6 in FIG. 5.

FIGS. 5 and 6 show another illustrative embodiment of the invention in which each segment of ring 10 between points 12 and 14 includes three portions (22a, b, and c in the upper segment as viewed in FIG. 6, and 24a, b, and c in the lower segment as viewed in that FIG.). FIGS. 5 and 6 show portions 22b and 24b having larger cross section than portions 22a, 22c, 24a, and 24c. If, as is one possibility, all portions are made of the same material or of materials with similar strengths, the larger cross section of portions 22b and 24b will tend to make those portions less laterally flexible than the other portions (i.e., portions 22a, 22c, 24a, and 24c). In that case, the wing portions (22a/24a and 22c/24c) of ring 10 will be more laterally flexible than connecting portions 22b and 24b. Another possibility is to make portions 22b and 24b from a material that is significantly different from the other portions of the ring. The material choice can be such that portions 22b and 24b are more laterally flexible than the other portions, or alternatively that portions 22b and 24b are less laterally flexible than the other portions.

Although FIGS. 5 and 6 show portions 22b and 24b of equal length and symmetrically located in their respective segments of ring 10, other choices can be made regarding these characteristics. For example, portions 22b and 24b can be of different lengths. Alternatively or in addition, one or both of portions 22b and 24b can be unsymmetrically located along the length of the respective ring segments between points 12 and 14.

Figure 7:
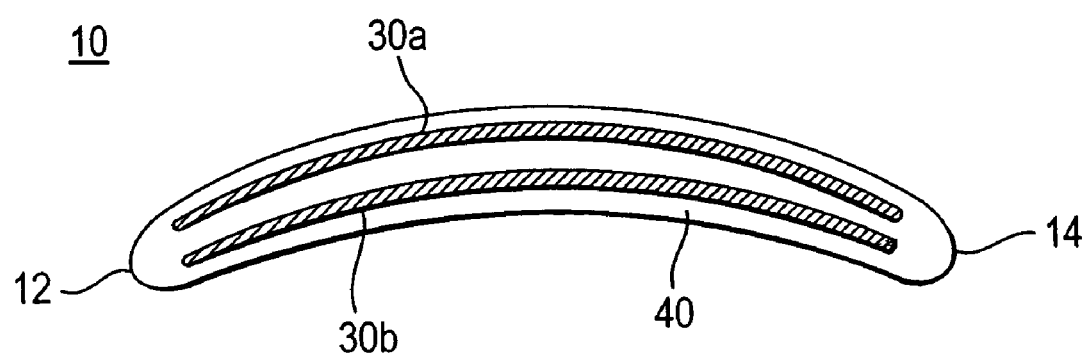
FIG. 7 is a view generally similar to FIG. 1 for another illustrative embodiment in accordance with the invention. However.

FIG. 7 shows yet another illustrative embodiment of the invention in which two wires 30a and 30b are embedded in a body 40 of elastomeric material (such as silicone) to form ring 10. Wire 30a is spaced above wire 30b in the z direction. However, this vertical spacing between wires 30 is less near points 12 and 14 than it is farther from those points. This tends to make ring 10 more laterally flexible adjacent to points 12 and 14, and less laterally flexible farther from points 12 and 14. In other words, the cross section of the ring is weaker in the vertical (z) direction where wires 30 are vertically closer together, and stronger where wires 30 are farther apart. The ring is less laterally (vertically) flexible where its cross section is thus structurally stronger. It is more laterally (vertically) flexible where its cross section is thus structurally weaker.

The construction shown in FIG. 7 is only one example of many types of generally similar constructions. For example, if it is desired to make the wings of the ring stiffer than the portion joining the wings, wires 30a and b can be made to be farther apart near points 12 and 14, and closer together farther from points 12 and 14. Another way to change the structural strength of various cross sections of the ring is to increase or decrease the number of wires like 30 as one proceeds annularly around the ring. Still another way to achieve this kind of result is to change the cross sectional size of one or more of wires 30 as one proceeds annularly around the ring.

To further clarify what is meant by lateral flexibility, a cantilevered element of a given length deflects laterally more in response to a given transverse force if it is more laterally flexible (or less laterally stiff). Conversely, a cantilevered element of a given length deflects laterally less in response to a given transverse force if it is less laterally flexible (or more laterally stiff).

Although different portions of the rings of this invention have different laterally flexibilities or stiffnesses, it will be understood that all portions of the rings are preferably sufficiently stiff to maintain the general shape of the ring (e.g., the depicted D and saddle shape), unless there is some purpose to be served by not maintaining these shape characteristics. To quantify the above-described saddle shape, when a ring of this invention is at rest (i.e., not subject to any external forces), the ratio of greatest height (in the z direction) to greatest width (in the x-y plane) is preferably in the range from about 5% to about 25%.

From the foregoing it will be seen that the invention can provide annuloplasty rings (e.g., for mitral valve repair and tricuspid valve repair) that have a saddle shape and the capability of flexing/displacing in all three axes (x, y, and z). Features of the device include the annuloplasty ring retaining its saddle shape in a dynamic system such as the heart, and also the ability to flex and move with the heart. Such a design is helpful in all mitral and tricuspid valve repairs, but especially for degenerative mitral valve repairs, where the surgeon tries to return the valve back to its natural anatomical shape.

In embodiments like those illustrated by FIGS. 1 and 2, dimensions x1 through x4 can be selected to produce desired amounts of flexing/displacement. For example, as noted earlier, x1 and x2 can be equal or unequal to achieve an equal or unequal displacement/flexing of the wings 22a/24a and 22e/24e. The flexing/displacement in the z direction ensures not only that the ring retains its saddle shape, but that it will also move naturally with the dynamic motion of the heart. For example, the ring may change from a flatter shape to a more saddle shape during diastolic-systolic shift. A structure in which all of dimensions x1 through x4 are equal can be used to achieve the same displacement of both wings. Alternatively, dimensional variations such as x1=x2, x1 not equal to x4, and x3=x4; or x1 not equal to x2, x1=x4, and x3 not equal to x4; etc., can be used to create an asymmetrical displacement of both wings if desired. This capability adds to the already flexible ring in the x and y axes. The ring can also have more than four flexible regions like 22b, 22d, 24b, and 24d to create the desired type of z-axis displacement.

Returning briefly to FIGS. 3 and 4, these FIGS. show one of the possible ways of accomplishing the z-axis displacement with changing cross-sectional geometry at the four flexible regions 22b, 22d, 24b, and 24d. The cross-section of the ring can be of any shape such as rectangular, circular, triangular, elliptical, etc., but preferably the dimensions at the flexible regions are smaller than the overall cross-sectional dimensions to provide the necessary displacement required. The cross-sectional dimensions at the flexible regions can be as small as possible to achieve greater displacement. The cross-sectional dimensions at each of the four flexible regions can be totally different to achieve the desired displacement required in the ring. The material used for such a design can be elgiloy, shape memory alloy, stainless steel, polymeric material, etc.

FIGS. 5 and 6 again show changing cross-sectional area. Instead of making the cross-sectional dimensions smaller at the four flexible regions as shown in FIGS. 3 and 4, the two central regions 22b and 24b are made larger/thicker. By varying the dimensions around these two central areas, the desired displacement can be effectively manipulated. The thicker areas may flex or move less compared to the thinner areas, thereby yielding the movement desired. This concept is highly effective if the device is molded or machined from the same polymeric material. This concept can, however, also work with different polymeric materials. For example, the thicker section of the ring can be molded from a tougher or higher durometer polymer compared to the wings 22a/24a and 22c/24c.

FIGS. 5 and 6 highlight another method of accomplishing all three axes displacements, especially in the z direction. This concept is to use two different materials if they are metallic. For example, the thicker region can be made out of material such as stainless steel, titanium, shape memory alloys, ceramic, etc., and the wing sections can be made out of shape memory alloys (such as nitinol) or other more elastic materials. The amounts that the wings are allowed to displace are directly influenced by the lengths A1 and A2 (FIGS. 5 and 6) of the thicker sections. The longer A1 or A2, the less displacement experienced by the wings. A1 and A2 can have dissimilar lengths to create the z-axis displacement desired. The same is true for the x and y axes.

FIG. 7 shows two shape memory alloys 30a and 30b (such as nitinol), formed into the desired saddle shape, and encapsulated by an elastomeric substrate 40 such as silicone. The two nitinol wires are separated by a vertical (z direction) gap. The amount of displacement in the z axis can be controlled by the dimensions of the cross-sectional profile of the shape memory alloy used. For example, if nitinol wire is used, the diameter of the wire can be varied to achieve the displacement desired. Displacement can also be controlled by the number of shape memory alloys encapsulated by the elastomeric substrate. By varying the number of encapsulated alloys, the cross-sectional dimensions of the alloy(s) (which do not need to be the same for each of the alloys), and the gap (vertical spacing) between the alloys, the overall x-y-z axes displacements can be controlled to yield the desired movements. The durometer of the elastomeric substrate can also be used as a variable to control displacements.

Physicians may select an appropriately sized three-dimensional ("3D") ring in accordance with this invention by using a 3D saddle-shaped sizer. Due to the varying size and shape of a given patient's mitral valve, various molded 3D saddle-shaped sizers can be used ensure that the physician selects the most appropriately sized annuloplasty ring. Additionally, such sizers will enable the physician to visualize how the ring will sit relative to the valve, and also where the sutures for securing the ring to the patient's tissue will go.

It will be understood that the foregoing is only illustrative of the principles of the invention, and that various modifications can be made by those skilled in the art without departing from the scope and spirit of the invention. For example, the number of portions of each segment between points 12 and 14 having different lateral flexibility can be different from the numbers of such portions shown in the illustrative embodiments. As another example of modifications within the scope of the invention, the D shape shown in the illustrative embodiments is only one example of possible ring shapes, and other shapes (e.g., oval shapes, elliptical shapes, shapes with no axis of symmetry, etc.) are equally possible. The drawings herein tend to show only the main structural members(s) of the depicted rings. It will be understood that rings within the scope of this invention may also have other components such as fabric covers.

The invention claimed is:

1. An annuloplasty ring having a resting shape when not subject to any forces and a longitudinal axis perpendicular to a plane parallel to a plan view of the ring, the ring comprising:
   first and second points on the ring that are spaced from one another in an annular direction around the ring, the first and second points lying in the plane parallel to the plan view of the ring;
   a first ring segment having a first midpoint and a second ring segment having a second midpoint, each ring segment extending from the first point to the second point, each ring segment arching upwardly out of the plane between the first and second points, and each ring segment including a plurality of annularly spaced portions that have different lateral flexibilities;
   a first relatively inflexible wing formed by at least one of the plurality of annularly spaced portions, wherein the first relatively inflexible wing extends from the first point along a portion of the first and second segments between a first end point located between the first point and the first midpoint and a second end point located between the first point and the second midpoint; and
   a second relatively inflexible wing formed by at least one of the plurality of annularly spaced portions, wherein the second relatively inflexible wing extends from the second point along a portion of the first and second segments between a third end point located between the second point and the first midpoint and a fourth end point located between the second point and the second midpoint, wherein the first and second points are the lowest points on the ring relative to the longitudinal axis, wherein:
   a shape of the ring changes from the resting shape to an other shape in response to application of a transverse force; and
   the shape of the ring returns to the resting shape from the other shape when the applied force is removed.

2. The ring defined in claim 1 wherein the portions have different cross sectional size to give them different lateral flexibilities.

3. The ring defined in claim 1 wherein the portions are made of different materials to give them different lateral flexibilities.

4. The ring defined in claim 1 wherein each of the segments includes first through fifth segment portions that are disposed in first through fifth order between the first and second points, and wherein the second and fourth segment portions are more laterally flexible than the first, third, and fifth segment portions.

5. The ring defined in claim 4 wherein the second and fourth segment portions have smaller cross section than the first, third, and fifth segment portions.

6. The ring defined in claim 4 wherein the second and fourth segment portions are made of material that is more laterally flexible than material of which the first, third, and fifth segment portions are made.

7. The ring defined in claim 1 wherein each of the segments includes first through third segment portions that are disposed in first through third order between the first and second points, and wherein the first and third segment portions are more laterally flexible than the second segment portions.

8. The ring defined in claim 7 wherein the first and third segment portions have smaller cross section than the second segment portions.

9. The ring defined in claim 7 wherein first and third segment portions are made of material that is more laterally flexible than material of which the second segment portions are made.

10. The ring defined in claim 1 wherein:
    the first segment comprises a first structural member extending axially along the first segment, the first structural member being substantially axially inflexible;
    the second segment comprises a second structural member extending axially along the second segment, the second structural member being substantially axially inflexible; and
    an elastic body encasing the first and second structural members.

11. The ring defined in claim 10 wherein, in each of the segments, spacing between the first and second structural members in a direction substantially perpendicular to the plane varies in a direction along the segment.

12. An annuloplasty ring comprising:
first and second points on the ring that are spaced from one another in an annular direction around the ring, the first and second points lying in a plane parallel to a plan view of the ring; and
first and second ring segments, each extending from the first point to the second point, each arching upwardly out of the plane between the first and second points, and each including a plurality of annularly spaced portions that have different lateral flexibilities, wherein at least three of the annularly spaced ring portions from the first and the second ring segments are disposed around the ring such that two of the at least three ring portions are relatively inflexible relative to a third of the at least three ring portions, wherein the two relatively inflexible ring portions are immediately adjacent to each other and only one of the two relatively inflexible ring portions is immediately adjacent to the third ring portion, and wherein the ring has a longitudinal axis perpendicular to the plane parallel to the plan view of the ring; the first ring segment having a first midpoint and the second ring segment having a second midpoint; and the ring further comprises a first relatively inflexible wing formed by at least one of the plurality of annularly spaced portions, wherein the first relatively inflexible wing extends from the first point along a portion of the first and second segments between a first end point located between the first point and the first midpoint and a second end point located between the first point and the second midpoint of the first and second ring segments, and a second inflexible wing formed by at least one of the plurality of annularly spaced portions, wherein the second relatively inflexible wing extends from the second point along a portion of the first and second segments between a third end point located between the second point and the first midpoint and a fourth end point located between the second point and the second midpoint, wherein the first and second points are the lowest points on the ring relative to the longitudinal axis.

13. The ring defined in claim 12 wherein the portions have different cross sectional size to give them different lateral flexibilities.

14. The ring defined in claim 12 wherein the portions are made of different materials to give them different lateral flexibilities.

15. The ring defined in claim 12 wherein each of the segments includes first through fifth portions that are disposed in first through fifth order between the first and second points, and wherein the second and fourth segment portions are more laterally flexible than the first, third, and fifth segment portions.

16. The ring defined in claim 15 wherein the second and fourth segment portions have smaller cross section than the first, third, and fifth segment portions.

17. The ring defined in claim 15 wherein the second and fourth segment portions are made of material that is more laterally flexible than material of which the first, third, and fifth segment portions are made.

18. The ring defined in claim 12 wherein each of the segments includes first through third portions that are disposed in first through third order between the first and second points, and wherein the first and third segment portions are more laterally flexible than the second segment portions.

19. The ring defined in claim 18 wherein the first and third segment portions have smaller cross section than the second segment portions.

* * * * *